(12) United States Patent
Huang et al.

(10) Patent No.: US 11,873,270 B2
(45) Date of Patent: Jan. 16, 2024

(54) ZN—AL SLURRY CATALYST, METHOD FOR PREPARING SAME AND APPLICATION IN PREPARING ETHANOL FROM SYNGAS

(71) Applicant: Taiyuan University of Technology, Shanxi (CN)

(72) Inventors: Wei Huang, Shanxi (CN); Jing Liu, Shanxi (CN); Jinchuan Fan, Shanxi (CN)

(73) Assignee: Taiyuan University of Technology, Shanxi (CN)

( * ) Notice: Subject to any disclaimer, the term of this patent is extended or adjusted under 35 U.S.C. 154(b) by 67 days.

(21) Appl. No.: 17/452,044

(22) Filed: Oct. 22, 2021

(65) Prior Publication Data

US 2022/0363618 A1 Nov. 17, 2022

(30) Foreign Application Priority Data

May 11, 2021 (CN) .......................... 202110508444.6

(51) Int. Cl.
*C07C 29/153* (2006.01)
*B01J 23/06* (2006.01)
(Continued)

(52) U.S. Cl.
CPC ............ *C07C 29/153* (2013.01); *B01J 21/02* (2013.01); *B01J 23/06* (2013.01); *B01J 37/033* (2013.01);
(Continued)

(58) Field of Classification Search
CPC ......... C07C 29/153; B01J 21/02; B01J 23/06; B01J 37/033; B01J 37/036; B01J 37/038;
(Continued)

(56) References Cited

U.S. PATENT DOCUMENTS

| 8,440,867 B1* | 5/2013 | Krause | .................. C07C 29/149 568/902.2 |
| 8,779,014 B2* | 7/2014 | Huang | .................... C07C 41/01 518/715 |

FOREIGN PATENT DOCUMENTS

CN 107262081 A * 10/2017

OTHER PUBLICATIONS

Scherer (Aging and drying of gels, Journal of Non-Crystalline Solids, 1988) (Year: 1988).*
(Continued)

*Primary Examiner* — Colin W. Slifka
*Assistant Examiner* — Logan Edward Laclair
(74) *Attorney, Agent, or Firm* — SALIWANCHIK, LLOYD & EISENSCHENK

(57) ABSTRACT

The present disclosure relates to the technical field of catalysts, and specifically to a Zn—Al slurry catalyst, its preparation method and its application in preparing ethanol from syngas. The preparation method provided in the disclosure prepares the Zn—Al slurry catalyst by introducing a zinc component into an aluminum sol, and the preparation method has a simple operation and a lower cost. The Zn—Al slurry catalyst prepared in the disclosure includes the Zn component and the Al component, which may catalyze syngas to generate ethanol under mild conditions. Also, the catalyst has stable properties, is not easy to be deactivated, and reduces the cost of preparing ethanol from syngas. When the Zn—Al slurry catalyst provided in the disclosure is used as the catalyst for preparing ethanol from syngas, the reaction conditions are mild, and the syngas may be catalyzed to generate ethanol under the conditions of 250-340° C. and 3-5 MPa.

5 Claims, 2 Drawing Sheets

(51) Int. Cl.
  *B01J 37/08* (2006.01)
  *B01J 37/03* (2006.01)
  *B01J 21/02* (2006.01)

(52) U.S. Cl.
  CPC ........... *B01J 37/036* (2013.01); *B01J 37/038* (2013.01); *B01J 37/08* (2013.01)

(58) Field of Classification Search
  CPC . B01J 37/08; B01J 37/031; B01J 21/04; B01J 37/082; Y02P 20/52
  See application file for complete search history.

(56) References Cited

OTHER PUBLICATIONS

You et al (Effects of Calcination on the Physical and Photocatalytic Properties of TiO2 Powders Prepared by Sol-Gel Template Method, Journal of Sol-Gel Science and Technology, 2005) (Year: 2005).*
Machine translation of CN-107262081-A (Year: 2017).*

* cited by examiner

ZN—AL SLURRY CATALYST, METHOD FOR PREPARING SAME AND APPLICATION IN PREPARING ETHANOL FROM SYNGAS

CROSS REFERENCE TO RELATED APPLICATION

This application claims the benefit of Chinese Application No. 202110508444.6, filed on May 11, 2021, which is hereby incorporated in its entirety.

TECHNICAL FIELD

The present disclosure relates to the technical field of catalysts, and specifically to a Zn—Al slurry catalyst, its preparation method and its application in preparing ethanol from syngas.

BACKGROUND ART

Because of the non-toxic and desirable physicochemical properties, ethanol is an important organic solvent, meanwhile, is a basic organic chemical raw material which may be used to prepare acetaldehyde, ethyl ether, ethyl acetate and other chemical products, and is also a raw material for making coatings, dyes, detergents and other products. Moreover, ethanol is generally acknowledged as a high-octane number pollution-free fuel additive. MTBE fuel additive, which seriously pollutes groundwater source, is gradually being eliminated. Once ethanol becomes a fuel additive actually, the demand for ethanol will be beyond estimation. On the other hand, due to the shortage of food and oil resources, the fermentation method and the petroleum-based ethylene hydration method for large-scale ethanol production face the challenge of cost and market price. Therefore, it is expected to solve the problem of the high cost of producing ethanol on a large scale through researching and developing the technical route of producing ethanol from syngas.

The catalysts used in the production of ethanol from syngas may be divided into three types: Rh-based catalysts, Mo-based catalysts and Cu-based catalysts. The space-time yield and selectivity of the Rh-based catalysts for ethanol are high, but due to the limited resource of Rh, the preparation cost of the catalyst is high, so it is difficult to realize industrialization. The Mo-based catalysts have a unique sulfur resistance and are not easy to accumulate carbon, and the products contain more alcohols and less water, but the reaction conditions are harsh, which are difficult to be achieved in actual production. The Cu-based catalysts include Cu—Co or Cu—Fe-based modified Fischer-Tropsch synthesis catalysts and Cu—Zn-based modified methanol catalysts, which have the advantages of low price and mild reaction conditions. However, the selectivity for ethanol of catalysts for producing ethanol from syngas is low, and the Cu-based catalysts are prone to deactivation with the progress of reaction.

In the long-term research process, researchers believe that Cu species is an indispensable active component in ethanol synthesis. Zuo et al. have studied the role of Cu clusters and Cu—O species adsorbed on ZnO surface in ethanol synthesis. They believe that the coexistence of $Cu^0$ and $Cu^+$ is necessary for the synthesis of $CH_3$ key intermediate. Zhang et al. consider that on Cu(110) crystal plane, the CO insertion into $CH_2$ is the main reaction of $C_2$ oxygenated compounds. On the Cu(211), $CH_3$ dissociated from $CH_3O$ is the most favorable monomer for CO insertion, and H assists CO dissociation with the lowest energy barrier, and CHO is thus most easily generated. Hofstadt et al. believe that $Cu^0$ is beneficial to the formation of $CH_2$ species, $Cu^+$ is beneficial to the formation of $CH_3O$ species, and $CH_3O$ and $CH_2$ may be combined to form ethanol. Wang et al. consider that the energy barrier of all steps of ethanol synthesis at the inclined crystal boundary of $Cu\Sigma5(310)$ is lower than that on the surface of Cu(111), because the crystal surface is more closely combined with all surface species, and the decrease in energy barrier of C—O bond breaking is the most obvious, which promotes the formation of $CH_2$. However, no matter in which mechanism, it is considered that Cu species is an essential active species.

SUMMARY

The present disclosure aims to provide a Zn—Al slurry catalyst, its preparation method and its application in preparing ethanol from syngas. The Zn—Al slurry catalyst provided in the disclosure may catalyze the syngas to prepare ethanol under mild conditions. Meanwhile, the Zn—Al slurry catalyst provided in the disclosure has the characteristics of stable properties and is not easy to be inactivated.

In order to achieve the above objects, the technical solutions of the present disclosure are specifically described as follows.

The disclosure provides a method for preparing a Zn—Al slurry catalyst, including:
  mixing an aluminum sol, a polyhydric alcohol and a zinc source solution to obtain a sol-gel precursor;
  performing successively an aging treatment and a heat treatment on the sol-gel precursor to obtain the Zn—Al slurry catalyst.

In some embodiments, a preparation process of the aluminum sol may include:
  mixing an aluminum salt with an aqueous solution of α-hydroxycarboxylic acid to obtain a suspension;
  performing successively a low temperature hydrolysis and a high temperature hydrolysis on the suspension to obtain the aluminum sol, where the low temperature hydrolysis is conducted at 35-55° C. for 2.5-3.5 h, and the high temperature hydrolysis is conducted at 85-100° C. for 0.5-1 h.

In some embodiments, the α-hydroxycarboxylic acid may include one or more selected from the group consisting of citric acid, lactic acid and glycolic acid; the aluminum salt may include aluminum isopropoxide and/or aluminum nitrate.

In some embodiments, a molar ratio of an aluminum element in the aluminum sol, the polyhydric alcohol and a zinc element in the zinc source may be 0.4-0.8:0.6-1.0:0.6-1.2.

In some embodiments, the aging treatment may be conducted at 10-30° C. for 3-10 days.

In some embodiments, the heat treatment may be conducted at 280-300° C. for 6-10 h; a heating rate to reach a temperature for the heat treatment may be 2-5° C./min; the heat treatment may be performed in an inert medium.

In some embodiments, the zinc source may include one or more selected from the group consisting of zinc nitrate, zinc oxide and basic zinc carbonate; the polyhydric alcohol may include ethylene glycol and/or glycerol.

A Zn—Al slurry catalyst prepared by the method above is also provided in the disclosure.

Use of the Zn—Al slurry catalyst above in preparing ethanol from syngas is also provided in the disclosure.

In some embodiments, a temperature for preparing ethanol from syngas may be 250-340° C.; a pressure for preparing ethanol from syngas may be 3-5 MPa.

The disclosure provides a method for preparing a Zn—Al slurry catalyst, which includes the following steps: mixing an aluminum sol, a polyhydric alcohol and a zinc source solution to obtain a sol-gel precursor; successively performing an aging treatment and a heat treatment on the sol-gel precursor to obtain the Zn—Al slurry catalyst. In the preparation method provided in the disclosure, the Zn component is introduced into the aluminum sol to thus prepare the Zn—Al slurry catalyst. The preparation method provided in the disclosure has a simple operation and a lower cost.

The disclosure also provides a Zn—Al slurry catalyst prepared by the above method. The Zn—Al slurry catalyst provided in the disclosure includes Zn component and Al component, which may catalyze syngas to prepare ethanol under mild conditions, and has stable properties and is not easy to be deactivated.

The disclosure also provides the application of the Zn—Al slurry catalyst above in preparing ethanol from syngas. In this disclosure, the Zn—Al slurry catalyst is used as a slurry catalyst for preparing ethanol from syngas, which breaks the existing understanding that Cu acts as the active site in an alcohol synthesis catalyst and an F-T constituent or alkali metal promoter has the chain growth ability. At the same time, the catalyst provided in the disclosure overcomes the problem of deactivation of traditional Cu-based catalysts, and reduces the cost of preparing ethanol from syngas in terms of catalyst. In addition, when the Zn—Al slurry catalyst provided in the disclosure is used as the catalyst for preparing ethanol from syngas, the reaction conditions are mild, and the syngas may be catalyzed to produce ethanol under the conditions of 250-340° C. and 3-5 MPa.

BRIEF DESCRIPTION OF THE DRAWINGS

In order to explain the embodiments of the present disclosure or the technical solutions in the prior art more clearly, the drawings that need to be used in the description of the embodiments will be briefly introduced below. Obviously, the drawings described below are only embodiments of the present disclosure. For those of ordinary skill in the art, other drawings may be obtained based on the drawings disclosed without creative work.

DETAILED DESCRIPTION OF THE EMBODIMENTS

Figure 1:
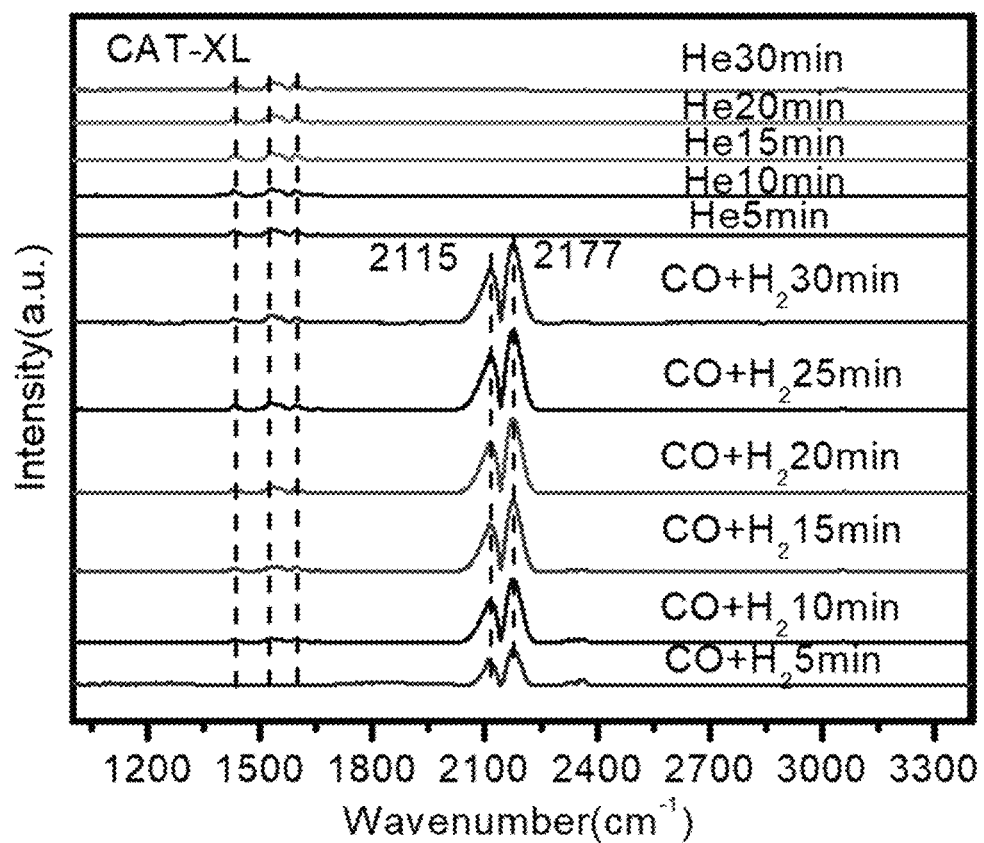
FIG. 1 is an in-situ infrared spectrum of the Zn—Al catalyst obtained in Example 2 at the wave number of 1000-3400 $cm^{-1}$.

The disclosure provides a method for preparing a Zn—Al slurry catalyst, which includes:
  mixing an aluminum sol, a polyhydric alcohol and a zinc nitrate solution to obtain a sol-gel precursor;
  performing successively an aging treatment and a heat treatment on the sol-gel precursor to obtain the Zn—Al slurry catalyst.

In the disclosure, the aluminum sol, the polyhydric alcohol and the zinc nitrate solution are mixed to obtain the sol-gel precursors. In the disclosure, the polyhydric alcohol preferably includes ethylene glycol and/or glycerol. The mass fraction of zinc element in the zinc source solution is preferably 0.10-0.86, and further preferably 0.45. The mass fraction of aluminum element in the aluminum sol is preferably 0.10-0.20, and further preferably 0.15. The molar ratio of the aluminum element in the aluminum sol, the polyhydric alcohol and the zinc element in the zinc source is preferably 0.4-0.8:0.6-1.0:0.6-1.2, and further preferably 0.8:0.8:1. The zinc source preferably includes one or more selected from the group consisting of zinc nitrate, zinc oxide and basic zinc carbonate, and further preferably zinc nitrate. The polyhydric alcohol preferably includes ethylene glycol and/or glycerol, and further preferably ethylene glycol.

In the present disclosure, a method for preparing the aluminum sol preferably includes the following steps: mixing an aluminum salt with an aqueous solution of α-hydroxycarboxylic acid to obtain a suspension; successively performing a low temperature hydrolysis and a high temperature hydrolysis on the suspension to obtain the aluminum sol. A temperature for the low temperature hydrolysis is preferably 35-55° C., and further preferably 40-50° C.; a time for the low temperature hydrolysis is preferably 2.5-3.5 h, and further preferably 3 h. A temperature for the high temperature hydrolysis is preferably 85-100° C., and further preferably 90-95° C.; a time for the high temperature hydrolysis is preferably 0.5-1 h, and further preferably 0.6-0.9 h. The α-hydroxycarboxylic acid preferably includes one or more selected from the group consisting of citric acid, lactic acid and glycolic acid. The aluminum salt includes aluminum isopropoxide and/or aluminum nitrate. The mass fraction of the α-hydroxycarboxylic acid aqueous solution is preferably 0.02-0.08, and further preferably 0.056. The molar ratio of the α-hydroxycarboxylic acid in the α-hydroxycarboxylic acid aqueous solution to the aluminum element in the aluminum salt is preferably 0.2-1.0:1, and further preferably 0.3:1. In the disclosure, the aluminum sol is prepared by the low temperature hydrolysis followed by the high temperature hydrolysis. In the process of low temperature hydrolysis, the hydrolysis reaction occurs to form aluminum hydroxide, and then in the process of high temperature hydrolysis, the dehydration polycondensation and the dealcoholization polycondensation reactions occur to form the aluminum sol at last.

After the sol-gel precursor is obtained, in the disclosure, the sol-gel precursor is subjected to an aging treatment and a heat treatment successively to obtain the Zn—Al slurry catalyst. In the disclosure, the temperature for the aging treatment is preferably 10-30° C., and the time for the aging treatment is preferably 3-10 days. The temperature for the heat treatment is preferably 280-300° C., further preferably 290-300° C., and most preferably 300° C., and the time for the heat treatment is preferably 6-10 h, and further preferably 7 h. The heating rate to reach the temperature for the heat treatment is preferably 2-5° C./min, further preferably 3-4° C./min, and more preferably 3° C. The heat treatment is preferably carried out in an inert medium, and the inert medium is preferably liquid paraffin. In the specific embodiments of the disclosure, the obtained sol-gel precursor is preferably added to liquid paraffin, heated to 290-300° C. at a heating rate of 3° C./min in a nitrogen atmosphere under atmospheric environment, and then subjected to heat preservation for 7 h to obtain the Zn—Al slurry catalyst. In the disclosure, the heat treatment on the sol-gel precursor obtained may ensure that the final preparation environment of the catalytic material is similar to the use environment thereof, so as to avoid the deactivation problem caused by such as an increased viscosity and a poor fluidity of the medium, due to the settlement of the prepared catalyst in the bed layer.

In the disclosure, the zinc component is introduced into the aluminum sol to prepare the Zn—Al slurry catalyst. The preparation method is simple in operation and lower in cost.

The disclosure also provides the Zn—Al slurry catalyst prepared by the above preparation method. The Zn—Al slurry catalyst provided in the disclosure includes the Zn component and the Al component, which may catalyze syngas to generate ethanol under mild conditions, and has stable properties and is not easy to be deactivated.

The disclosure also provides the application of the Zn—Al slurry catalyst above in preparing ethanol from syngas. The specific method of the application is not specially required, and the ones well-known by those skilled in the art may all be used. In the disclosure, the temperature for the application is preferably 250-340° C., and the pressure is preferably 3-5 MPa. The composition of the syngas includes carbon monoxide and hydrogen. In the disclosure, the Zn—Al slurry catalyst is used as a slurry catalyst for preparing ethanol from syngas, which breaks the existing understanding that Cu is the active site in an alcohol synthesis catalyst and a F-T constituent or alkali metal promoter has the chain growth ability. At the same time, the catalyst provided in the disclosure overcomes the problem of deactivation of traditional Cu-based catalysts and reduces the cost of preparing ethanol from syngas. In addition, when the Zn—Al slurry catalyst provided in the disclosure is used as the catalyst for preparing ethanol from syngas, the reaction conditions are mild, and the syngas may be catalyzed to produce ethanol under the conditions of merely 280° C. and 4 MPa. In the disclosure, the Zn—Al slurry catalyst is applied to a slurry bed and a fixed bed in the application process of preparing ethanol from syngas. When applied to a fixed bed, the Zn—Al slurry catalyst is required to be pyrolyzed. The pyrolyzing process includes: standing and centrifuging the slurry Zn—Al catalyst to obtain a precipitated part; drying and placing the precipitated part into a tubular furnace, heating to 800° C. at the rate of 2° C./min, and then keeping for 5 h. A solid catalyst is thus obtained, which may be applied to the fixed bed. When applied to the slurry bed, the Zn—Al slurry catalyst may be used directly without pyrolysis.

In order to further illustrate the present disclosure, the Zn—Al slurry catalyst provided in the disclosure will be described in detail below in combination with the drawings and the embodiments, which, however, should not be understood as limitations to the protection scope of the disclosure.

Example 1

5.12 g of citric acid was dissolved in 86.5 ml of deionized water and then heated to 50° C. Aluminum isopropoxide was added, hydrolyzed for 3 h, and then heated to 95° C. and hydrolyzed for 1 h to obtain an aluminum sol. 55.64 mL of ethylene glycol was added dropwise into the obtained aluminum sol. After 30 minutes, 5 ml of water solution containing 29.75 g of zinc nitrate was added and stirred to form a viscous sol-gel precursor. The obtained sol-gel precursor was aged at room temperature for 10 days. The inert medium of liquid paraffin was used as the heat treatment medium. Under the conditions of atmospheric pressure and nitrogen protection, the resultant was heated to 300° C. at a heating rate of 3° C./min, and was subjected to heat treatment for 7 h after the temperature reached 300° C. A Zn—Al slurry catalyst was obtained.

The activity of the Zn—Al slurry catalyst above was evaluated in a slurry bed at 280° C. and 4 MPa using the syngas with a volume ratio of carbon monoxide to hydrogen of 1:2 as a raw material. The gas phase products were detected online by gas chromatography, and the liquid phase products were detected by manual injection. Finally, the activity evaluation data of the catalyst was obtained. The results are shown in Table 1. Table 1 is the activity evaluation table of the catalyst obtained in Example 1.

TABLE 1

Activity evaluation table of the catalyst in Example 1

| Temper (° C.) | Reaction time/(d) | X(CO)/% | EtOH/ROH/% | Product selectivity (c-mol)/% | | | | | |
|---|---|---|---|---|---|---|---|---|---|
| | | | | MeOH | EtOH | $C_{3+}OH$ | DME | $CO_2$ | CH |
| 280 | 1 | 4.13 | 44.75 | 6.40 | 3.80 | 0.17 | 0.45 | 1.25 | 87.93 |
| | 2 | 4.95 | 63.92 | 6.21 | 11.82 | 1.77 | 0.34 | 0.92 | 78.94 |
| | 3 | 4.81 | 60.35 | 5.38 | 11.69 | 2.89 | 0.27 | 3.99 | 75.78 |
| | 4 | 5.00 | 59.65 | 5.58 | 12.61 | 3.43 | 0.35 | 5.32 | 72.71 |
| | 5 | 5.47 | 52.92 | 5.30 | 10.05 | 3.79 | 0.07 | 8.50 | 72.29 |
| | 6 | 4.96 | 58.88 | 6.04 | 11.77 | 2.95 | 0.51 | 3.33 | 75.40 |

It may be seen from Table 1 that the CO conversion rate of the Zn—Al catalyst obtained in Example 1 is 5%. The first day is an activation period, and the evaluation results of the second to the sixth day are stable, where the proportions of ethanol in total alcohol are all over 50%, and no obvious deactivation appears.

Example 2

5.12 g of citric acid was dissolved in 86.5 ml of deionized water and then heated to 50° C. Aluminum isopropoxide was added, hydrolyzed for 3 h, and then heated to 95° C. and hydrolyzed for 1 h to obtain an aluminum sol. 55.64 mL of ethylene glycol was added dropwise into the obtained aluminum sol. After 30 minutes, 5 ml of water solution containing 29.75 g of zinc nitrate was added and stirred to form a viscous sol-gel precursor. The obtained sol-gel precursor was aged at room temperature for 10 days. The inert medium of liquid paraffin was used as the heat treatment medium. Under the conditions of atmospheric pressure and nitrogen protection, the resultant was heated to 300° C. at a heating rate of 3° C./min, and was subjected to heat treatment for 7 h after the temperature reached 300° C. A Zn—Al slurry catalyst was obtained.

The Zn—Al slurry catalyst obtained was stood and centrifuged. A precipitated part was dried, then placed into a tubular furnace to be heated to 800° C. at the rate of 2° C./min, and kept for 5 h, so that the solid catalyst was obtained. The precursor prepared by the sol-gel method as provided in Example 2 of the present disclosure was heat-treated with paraffin as a medium. The paraffin might decompose into C and H substances at a high temperature, resulting in excess carbon content on the surface of the catalyst. Therefore, if the catalyst was directly used in the fixed bed for an activity evaluation, it might not be active due to the active sites thereof being wrapped. Thus, the catalyst was pyrolyzed in the tubular furnace to expose more active sites, so as to ensure the accuracy of the final determination results.

The activity of the catalyst was evaluated in a fixed bed reactor using the syngas as a raw material. In this activity evaluation, four reaction temperatures were used. The gas phase products were detected online by the gas chromatography, and the liquid phase products were detected by manual injection. Finally, the activity evaluation data of the catalyst was obtained. The results are shown in Table 2. Table 2 is the activity evaluation table of the catalyst obtained in Example 2.

of the Zn—Al catalyst obtained in Example 2 at the wave number of 1000-1700 cm$^{-1}$. It may be seen from FIG. 1 that there are absorption peaks at 2115 cm$^{-1}$ and 2117 cm$^{-1}$ on the surface of the catalyst, but the absorption peaks disappear after purging with He, which indicates that the absorption peaks on the surface of the catalyst may be attributed to the gaseous CO. The peaks related to formic acid (vaO—C—O 1596 cm$^{-1}$) and acetate (vaO—C—O 1531 cm$^{-1}$) may be clearly observed from FIG. 2. Meanwhile, the bands at 1452 cm$^{-1}$ and 1430 cm$^{-1}$ in FIG. 2 may be attributed to methoxy ($CH_3O$) and bidentate chelated methoxy ($\delta CH$). Therefore, the route of ethanol synthesis by the catalyst obtained in Example 2 may be that the formate interacts with the methyl group derived from the surface methoxyl group to form the acetate, which further forms ethanol.

Comparative Example 1

5.12 g of citric acid was dissolved in 86.5 ml of deionized water and then heated to 50° C. Aluminum isopropoxide was added, hydrolyzed for 3 h, and then heated to 95° C. and hydrolyzed for 1 h to obtain an aluminum sol. 55.64 mL of ethylene glycol solution containing 48.32 g of copper nitrate was added dropwise into the obtained aluminum sol. After 30 minutes, 5 ml of water solution containing 29.75 g of zinc nitrate was added and stirred to form a viscous sol-gel precursor. The obtained sol-gel precursor was aged at room

TABLE 2

Activity evaluation table of the catalyst in Example 2

| Temper/ °C. | Reaction time/d | X(CO)/% | EtOH/ ROH/% | Product selectivity (c-mol)/% | | | | | |
|---|---|---|---|---|---|---|---|---|---|
| | | | | MeOH | EtOH | $C_{3+}$OH | DME | $CO_2$ | CH |
| 280 | 2 | 4.33 | 43.9 | 8.59 | 4.66 | 2.07 | 0.04 | 3.92 | 80.72 |
| | 3 | 3.62 | 41.4 | 8.04 | 4.23 | 1.45 | 0.97 | 2.64 | 82.67 |
| 300 | 4 | 8.95 | 45.8 | 11.05 | 6.45 | 2.71 | 0.05 | 4.59 | 75.15 |
| | 5 | 7.58 | 44.9 | 10.05 | 5.70 | 2.50 | 0.11 | 4.77 | 76.87 |
| | 6 | 7.05 | 44.8 | 10.12 | 5.75 | 2.45 | 0.10 | 4.38 | 77.20 |
| 320 | 7 | 14.03 | 41.9 | 8.70 | 5.25 | 1.03 | 0.14 | 6.62 | 78.26 |
| | 8 | 11.67 | 44.1 | 8.64 | 5.27 | 1.55 | 0.12 | 5.58 | 78.84 |
| | 9 | 12.08 | 45.1 | 10.31 | 6.05 | 2.42 | 0.05 | 1.79 | 79.38 |
| 340 | 10 | 20.66 | 43.1 | 6.23 | 3.26 | 1.46 | 0.11 | 11.83 | 77.11 |

It may be seen from Table 2 that with the increase in temperature, the conversion of CO is increased. When the temperature reaches 340° C., the conversion may be up to 20% or more, but the selectivity for the by-product $CO_2$ is improved. Therefore, when the reaction temperature is 320° C., the catalyst obtained in Example 2 of the disclosure has the most excellent catalytic performance of catalyzing with a fixed bed, where the conversion is increased to 10% or more, and the proportions of ethanol in total alcohol are still maintained at 40% or more.

Figure 2:
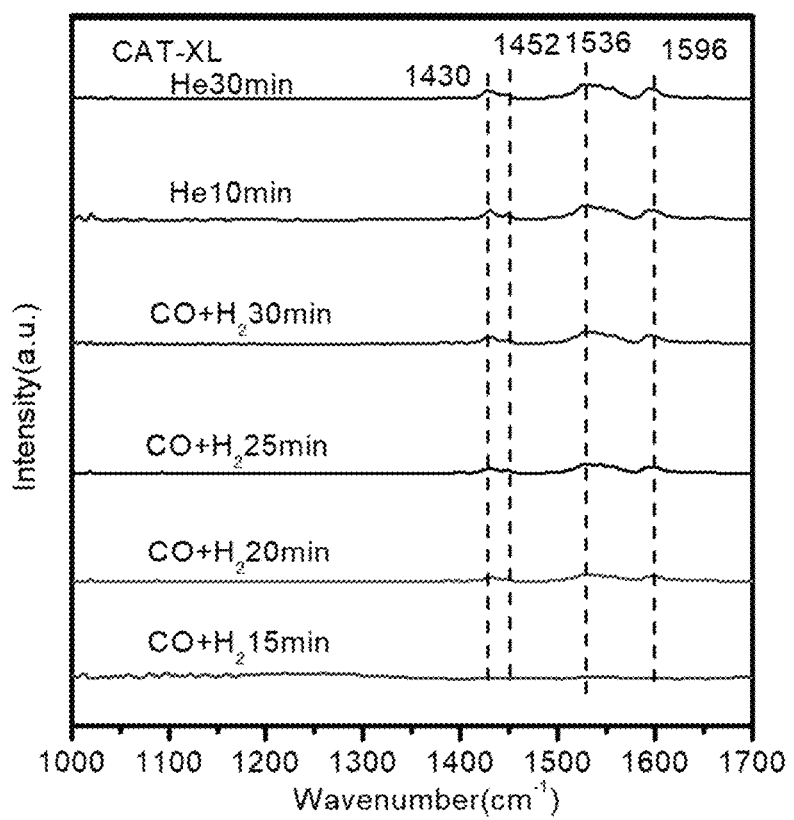
FIG. 2 is an in-situ infrared spectrum of the Zn—Al catalyst obtained in Example 2 at the wave number of 1000-1700 $cm^{-1}$.

In the process of feeding syngas, the in-situ infrared scanning was carried out on the surface of the catalyst obtained in Example 2, and the results are shown in FIG. 1 and FIG. 2. FIG. 1 is the in-situ infrared spectrum of the Zn—Al catalyst obtained in Example 2 at wave number of 1000-3400 cm$^{-1}$, and FIG. 2 is the in-situ infrared spectrum temperature for 10 days. The inert medium of liquid paraffin was used as the heat treatment medium. Under the conditions of atmospheric pressure and nitrogen protection, the resultant was heated to 300° C. at a heating rate of 3° C./min, and was subjected to heat treatment for 7 h after the temperature reached 300° C. A Cu—Zn—Al slurry catalyst was obtained.

Under a pressure of 4 MPa, the activity of the catalyst was evaluated in a slurry bed using 250° C. and 280° C. as the catalytic temperatures respectively and the syngas as the raw material. The gas phase products were detected online by the gas chromatography, and the liquid phase products were detected by manual injection. Finally, the activity evaluation data of the catalyst was obtained. The results are shown in Table 3. Table 3 is the activity evaluation table of the catalyst obtained in Example 3.

TABLE 3

Activity evaluation table of the catalyst

| Temper/ (° C.) | Reaction time/d | X(CO)/% | $C_{2+}OH/$ ROH | Product selectivity (c-mol)/% | | | | | | ROH distribution/%(wt) | | | |
|---|---|---|---|---|---|---|---|---|---|---|---|---|---|
| | | | | MeOH | EtOH | $C_{3+}OH$ | DME | $CO_2$ | CH | MeOH | EtOH | PrOH | BuOH |
| 250 | 1 | 2.36 | 44.21 | 16.83 | 9.28 | 0.00 | 43.82 | 8.29 | 21.77 | 55.79 | 44.21 | 0.00 | 0.00 |
| | 2 | 2.42 | 25.82 | 20.46 | 4.95 | 0.00 | 39.24 | 15.25 | 20.09 | 74.18 | 25.82 | 0.00 | 0.00 |
| | 3 | 2.37 | 29.76 | 30.75 | 8.00 | 0.78 | 21.21 | 21.30 | 17.96 | 70.24 | 26.26 | 2.72 | 0.78 |
| 280 | 4 | 7.33 | 62.50 | 9.55 | 9.41 | 1.19 | 1.08 | 40.03 | 38.74 | 37.50 | 53.15 | 6.30 | 3.06 |
| | 5 | 7.01 | 79.89 | 10.12 | 23.40 | 36.76 | 4.59 | 11.47 | 47.18 | 20.11 | 66.86 | 8.03 | 5.00 |
| | 6 | 10.12 | 71.06 | 8.88 | 12.26 | 23.33 | 7.99 | 34.16 | 34.52 | 28.60 | 56.91 | 8.91 | 5.59 |
| | 7 | 9.86 | 60.07 | 12.36 | 10.05 | 24.49 | 13.06 | 24.10 | 38.35 | 39.93 | 46.64 | 9.07 | 4.36 |

It may be seen from Table 3 that when the reaction temperature is 250° C., the catalyst has a CO conversion of only about 2%, and has a certain ability to generate ethanol. Under 280° C., the selectivity for ethanol is as high as 23% in the second day. However, from the third day, the selectivity for ethanol drops sharply to 12%. It may be seen that the deactivation rate of the Cu—Zn—Al catalyst is as high as 47% in the third day.

It may be known from the above embodiments that the Zn—Al slurry catalyst provided in the disclosure may catalyze the ethanol preparation from syngas under mild conditions, and has the characteristics of high property stability and low deactivation compared with the Cu-based catalyst.

Although the above embodiments have described the present disclosure in detail, they are only a part of, rather than all of, the embodiments in the disclosure. Other embodiments may also be obtained according to the embodiments disclosed without creative work. All of these embodiments should fall within the scope of the disclosure.

What is claimed is:

1. A method for preparing a Zn—Al slurry catalyst, comprising:
   mixing an aluminum sol, a polyhydric alcohol, and a zinc source solution to obtain a sol-gel precursor; and
   performing successively an aging treatment and a heat treatment on the sol-gel precursor to obtain the Zn—Al slurry catalysts,
   wherein the aging treatment is conducted at 10-30° C. for 3-10 days,
   wherein the heat treatment is conducted at 280-300° C. for 6-10 h,
   wherein a heating rate to reach a temperature for the heat treatment is 2-5° C./min,
   wherein the heat treatment is performed in an inert medium, and
   wherein the inert medium is liquid paraffin.

2. The method according to claim 1, wherein a preparation process of the aluminum sol comprises:
   mixing an aluminum salt with an aqueous solution of α-hydroxycarboxylic acid to obtain a suspension; and
   performing successively a low temperature hydrolysis and a high temperature hydrolysis on the suspension to obtain the aluminum sol, wherein the low temperature hydrolysis is conducted at 35-55° C. for 2.5-3.5 h, and the high temperature hydrolysis is conducted at 85-100° C. for 0.5-1 h.

3. The method according to claim 2, wherein the α-hydroxycarboxylic acid comprises one or more selected from the group consisting of citric acid, lactic acid, and glycolic acid; and the aluminum salt comprises aluminum isopropoxide and/or aluminum nitrate.

4. The method according to claim 1, wherein a molar ratio of an aluminum element in the aluminum sol, the polyhydric alcohol, and a zinc element in the zinc source is 0.4-0.8:0.6-1.0:0.6-1.2.

5. The method according to claim 1, wherein the zinc source comprises one or more selected from the group consisting of zinc nitrate, zinc oxide, and basic zinc carbonate; and the polyhydric alcohol comprises ethylene glycol and/or glycerol.

* * * * *